(12) United States Patent
Repka et al.

(10) Patent No.: US 10,154,129 B2
(45) Date of Patent: Dec. 11, 2018

(54) WEARABLE ELECTRONIC APPARATUS

(71) Applicant: POLAR ELECTRO OY, Kempele (FI)

(72) Inventors: Mikko Repka, Oulu (FI); Mika Erkkila, Oulu (FI)

(73) Assignee: Polar Electro Oy, Kempele (FI)

( * ) Notice: Subject to any disclaimer, the term of this patent is extended or adjusted under 35 U.S.C. 154(b) by 0 days.

(21) Appl. No.: 14/713,727

(22) Filed: May 15, 2015

(65) Prior Publication Data

US 2016/0337843 A1    Nov. 17, 2016

(51) Int. Cl.
| | |
|---|---|
| *H04M 1/725* | (2006.01) |
| *H04L 12/58* | (2006.01) |
| *H04W 8/22* | (2009.01) |
| *G06F 9/451* | (2018.01) |
| *A61B 5/024* | (2006.01) |
| *A61B 5/11* | (2006.01) |
| *G06F 1/16* | (2006.01) |
| *G06F 3/01* | (2006.01) |
| *G06F 9/54* | (2006.01) |
| *G06F 3/0346* | (2013.01) |

(Continued)

(52) U.S. Cl.
CPC ..... *H04M 1/72569* (2013.01); *A61B 5/02438* (2013.01); *A61B 5/1118* (2013.01); *G06F 1/163* (2013.01); *G06F 3/014* (2013.01); *G06F 3/017* (2013.01); *G06F 3/0346* (2013.01); *G06F 9/451* (2018.02); *G06F 9/542* (2013.01); *H04L 51/12* (2013.01); *H04L 51/24* (2013.01); *H04M 1/7253* (2013.01); *H04M 1/72563* (2013.01); *H04M 1/72577* (2013.01); *H04W 8/22* (2013.01);

*A61B 5/01* (2013.01); *A61B 5/02405* (2013.01); *A61B 5/02416* (2013.01); *A61B 5/1112* (2013.01); *A61B 5/1123* (2013.01); *A61B 5/681* (2013.01); *A61B 5/6823* (2013.01); *A61B 5/6824* (2013.01); *A61B 5/6829* (2013.01); *A61B 2503/10* (2013.01); *A61B 2562/0219* (2013.01); *H04L 51/32* (2013.01)

(58) Field of Classification Search
CPC .......... H04W 8/22; H04W 4/12; H04W 4/14; H04W 8/24; H04M 2250/52; H04M 1/72563; H04M 1/72569; H04M 2250/12; H04M 1/6075; H04M 1/6091; H04M 1/72522; H04M 1/72527
See application file for complete search history.

(56) References Cited

U.S. PATENT DOCUMENTS 8,825,836 B1    9/2014 Gibson et al.
2010/0211575 A1*  8/2010 Collins ............. G06F 17/30044
                                                  707/749

(Continued)

FOREIGN PATENT DOCUMENTS

WO    2015/024674 A1    2/2015

*Primary Examiner* — Magdi Elhag
(74) *Attorney, Agent, or Firm* — FisherBroyles, LLP

(57) ABSTRACT

A wearable electronic apparatus, a computer program and a method are disclosed. Physical activity data measured relating to a user of a wearable electronic apparatus is obtained. An exercise mode of the wearable electronic apparatus is switched on such that information related to the physical activity data is outputted to the user. While the exercise mode is on, wireless application data is received, and, only if the application data fulfills a predetermined relevance condition, the application data is outputted to the user.

22 Claims, 7 Drawing Sheets

(51) Int. Cl.
*A61B 5/00* (2006.01)
*A61B 5/01* (2006.01)

(56) References Cited

U.S. PATENT DOCUMENTS

| | | | | |
|---|---|---|---|---|
| 2013/0106603 | A1* | 5/2013 | Weast | G06F 1/163 340/539.11 |
| 2014/0344375 | A1 | 11/2014 | Hauser et al. | |
| 2014/0347265 | A1* | 11/2014 | Aimone | G09G 3/003 345/156 |
| 2015/0187188 | A1* | 7/2015 | Raskin | G08B 6/00 340/407.1 |
| 2015/0358357 | A1* | 12/2015 | Diaz-Tellez | G06F 21/6209 726/27 |
| 2016/0071390 | A1* | 3/2016 | Sales | A61B 5/1114 340/573.1 |

\* cited by examiner

WEARABLE ELECTRONIC APPARATUS

BACKGROUND

Field

The invention relates to a wearable electronic apparatus, a computer program and a method.

Description of the Related Art

Usability of a wearable electronic apparatus may be compromised for various reasons. A user interface may be challenged with excess information, for example. A battery life may also be shortened due to processing of needless information, for example.

SUMMARY

According to an aspect of the present invention, there is provided a wearable electronic apparatus comprising: a user interface; a radio transceiver; a sensor interface; one or more processors; and one or more memories including computer program code, the one or more memories and the computer program code configured to, with the one or more processors, cause the apparatus at least to: obtain, with the sensor interface, physical activity data measured relating to a user of the wearable electronic apparatus; switch an exercise mode of the apparatus on such that information related to the physical activity data is outputted, with the user interface, to the user; and, while the exercise mode is on, receive, with the radio transceiver, application data, and, only if the application data fulfills a predetermined relevance condition, output, with the user interface, the application data to the user.

According to another aspect of the present invention, there is provided a non-transitory computer-readable storage medium comprising a computer program comprising computer program code which, when loaded into a wearable electronic apparatus cause the apparatus at least to: obtain physical activity data measured relating to a user of the wearable electronic apparatus; switch an exercise mode of the wearable electronic apparatus on such that information related to the physical activity data is outputted to the user; and, while the exercise mode is on, receive wireless application data, and, only if the application data fulfills a predetermined relevance condition, output the application data to the user.

According to another aspect of the present invention, there is provided a method comprising: obtaining physical activity data measured relating to a user of a wearable electronic apparatus; switching an exercise mode of the wearable electronic apparatus on such that information related to the physical activity data is outputted to the user; and, while the exercise mode is on, receiving wireless application data, and, only if the application data fulfills a predetermined relevance condition, outputting the application data to the user.

According to another aspect of the present invention, there is provided a method comprising: obtaining physical activity data measured relating to a user of a wearable electronic apparatus; switching an exercise mode of the wearable electronic apparatus on such that information related to the physical activity data is outputted to the user; and, while the exercise mode is on, if a predetermined transmit condition is fulfilled, transmitting wirelessly the information related to the physical activity data to an electronic social media service.

BRIEF DESCRIPTION OF THE DRAWINGS

Example embodiments of the present invention are described below, by way of example only, with reference to the accompanying drawings, in which.

DETAILED DESCRIPTION

The following embodiments are only examples. Although the specification may refer to "an" embodiment in several locations, this does not necessarily mean that each such reference is to the same embodiment(s), or that the feature only applies to a single embodiment. Single features of different embodiments may also be combined to provide other embodiments. Furthermore, words "comprising" and "including" should be understood as not limiting the described embodiments to consist of only those features that have been mentioned and such embodiments may contain also features/structures that have not been specifically mentioned.

Figure 1:
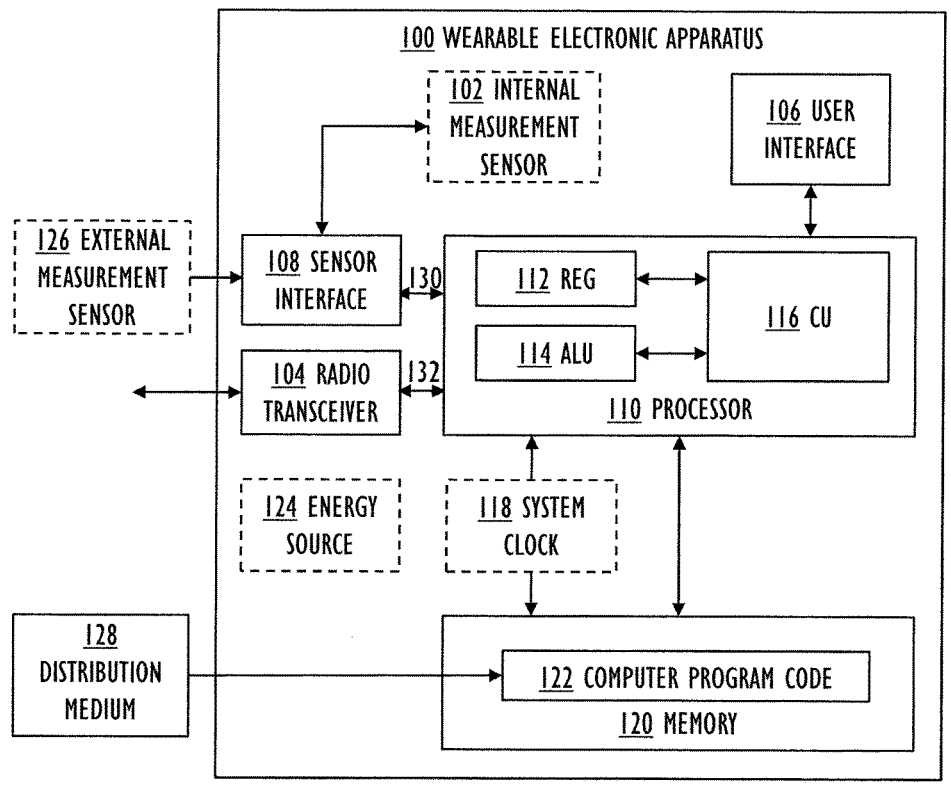
FIGS. 1, 2, 3 and 4 illustrate example embodiments of a wearable electronic apparatus.

FIG. 1 illustrates example embodiments of a wearable electronic apparatus 100. It should be noted that while FIG. 1 illustrates various example embodiments of the apparatus 100, it is only a simplified block diagram that only shows some structures and functional entities. The connections shown in FIG. 1 are logical connections; the actual physical connections may be different. It is apparent to a person skilled in the art that the described apparatus 100 may also comprise other functions and structures. It should be appreciated that details of some functions, structures, and the protocols used for communication are irrelevant to the actual invention. Therefore, they need not be discussed in more detail here.

The apparatus 100 comprises a user interface 106, a radio transceiver 104, a sensor interface 108, one or more processors 110, and one or more memories 120 including computer program code 122.

The sensor interface 108 may be utilized to obtain physical activity data 130 measured relating to a user of the apparatus 100.

In an example embodiment, the apparatus 100 may further comprise one or more internal measurement sensors 102, and/or the apparatus 100 may be communicatively coupled with one or more external measurement sensors 126.

As illustrated in FIG. 1, the sensors 102, 126 may be internal measurement sensors 102 (within the apparatus 100) and/or (wireless) external measurement sensors 126 (outside of the apparatus 100). The apparatus 100 may comprise, as the sensor interface 108, a transceiver for communicating with the wireless external measurement sensor(s) 126, or even just a receiver for receiving measurements from the wireless external measurement sensors 126. For the internal measurement sensors 102, the interface 108 may be a suitable hardware communication interface such as a wired interface or an appropriate communication bus, for example.

The sensor(s) 102, 126 may produce the physical activity data 130 from user's physical activity such as sports-, exercise-, or activity-related data.

The following is a non-limiting list of possible types of the physical activity data 130 (also known as physiological sensor data or exercise data) that may be detected by the sensors 102, 126 or that the apparatus 100 may determine on the basis of the physical activity data: heart rate zones, heart rate samples, heart rate variation samples, heart beat interval samples, fat consumption rate, calorie consumption rate, consumed amount of calories, activity zones, activity samples, speed and/or pace samples, power samples, cadence samples, altitude samples, temperature samples, location samples, distance elapsed, time elapsed, pedal index, left-right balance, running index, training load, galvanic skin response samples, fluid balance, skin temperature samples, heading samples and/or bike angles. The location data may comprise satellite positioning data, such as, GPS positioning data, or any other data that allows the determination of the location of the exerciser during the exercise at any given time. The movement indoors may be detected via indoor location tracking methods, such as mapping techniques including measuring Earth's magnetic fields or radio frequency signals.

A non-exhaustive list of sensors 102, 126 includes heart activity sensors, motion sensors, location sensors, swimming sensors and bike sensors, as well as other sensors gathering information regarding the training. Besides these, sensors 102, 126 may comprise any sensors that are needed for detecting a given exercise data type, such as temperature sensor for detecting ambient temperature or skin temperature.

The heart activity sensors may be configured to determine heart activity, such as heart rate, Heart Beat Interval (HBI) and/or Heart Rate Variability (HRV), for example. The heart activity sensors include, but are not limited to, a cardiovascular sensor (such as an electrocardiogram ECG sensor), an optical heart activity sensor such as a PPG (photoplethysmography) sensor, or a bioimpedance plethysmography. The optical heart activity sensor may detect the heart activity of the user by optical heart rate measurement, which may comprise sending a light beam towards skin of the user and measuring the bounced and/or emitted light from the skin of the user. The light beam may alter when travelling through veins of the user and the alterations may be detected by the optical heart rate activity sensor. Further, besides these types of heart activity sensors, also other types of biosignal measurement sensors may be embedded into the heart activity sensors. These types include but are not limited to the following: a Laser Doppler-based blood flow sensor, a magnetic blood flow sensor, an Electromechanical Film (EMFi) pulse sensor, a polarization blood flow sensor. In an example embodiment, the heart activity sensor may produce raw measurement data of the heart activity and/or it may process the measurement data into heart activity information, such as heart rate for example. This means that the sensor(s) 102, 120 in general may comprise data processing capabilities. Further, the raw measurement data and/or processed information may be processed by the apparatus 100 and/or transmitted to an external device, such as a portable apparatus 202, or even to a user web service 212, as will be explained later.

Motion sensors may be configured to measure motion induced by the user to the apparatus 100 by moving hand (or other body parts such as chest or ankle to which the motion sensor is attached to). The motion sensor may use other motion data, such as location data of the user, to determine motion of the user. In an example embodiment, the motion sensor comprises at least one of the following: an accelerometer, a magnetometer, and a gyroscope. The motion sensor may further comprise sensor fusion software for combining the accelerometer data and gyroscope data so as to provide physical quantities, such as acceleration data, velocity data, or limb trajectory data in a reference coordinate system having orientation defined by a predetermined gyroscope orientation.

Location sensors may utilize GPS (Global Positioning System) or other satellite-based, or radio system-based system for locating the user and measuring various parameters (speed, distance, location, route) relating to the movement of the user.

Swimming sensors may measure swimming specific parameters such as number of strokes or distance, for example.

Bike sensors may be sensors attached to various parts of the bike for measuring speed, cadence, or power, for example.

The gathered sensor information may be utilized to calculate further physical activity data of the user such as a total energy consumption, an energy consumption speed, an activity level, a cumulated activity, for example.

The radio transceiver 104 may comprise a cellular radio transceiver and/or a non-cellular radio transceiver. In an example embodiment, the cellular radio transceiver 104 may be interoperable with various wireless standard/non-standard/proprietary cellular radio networks 210 such as any mobile phone network, which may be coupled with a wired network such as the Internet.

In an example embodiment, the wireless communication network 210 comprises any mobile phone network, regardless of the generation (such as 2G, 3G, 4G, beyond 4G, 5G etc.) such as GSM (Global System for Mobile Communications), GPRS (General Packet Radio Service), EGPRS (Enhanced GPRS), WCDMA (Wideband Code Division Multiple Access), UMTS (Universal Mobile Telephone System), 3GPP (The 3rd Generation Partnership Project), IMT (International Mobile Telecommunication), LTE (Long Term Evolution, LTE-A (LTE-Advanced), Mobile WiMAX, and other radio systems (in their present forms and/or in their evolution forms).

In an example embodiment, the communication network 210 supports the use of subscriber identity module (SIM), which may be an integrated circuit storing subscriber data, which is network-specific information used to authenticate and identify the subscriber on the cellular network. The subscriber identity module may be embedded into a removable SIM card. Consequently, the apparatus 100 may include the SIM card (and a SIM card reader). Alternatively, the apparatus 100 may include a virtual or software SIM card.

In an example embodiment, the wireless communication network 210 comprises a wireless local area network (WLAN), a hotspot, or an access point, all of which may provide Internet access through the use of a router connected to a link to an Internet service provider.

In an example embodiment, the non-cellular radio transceiver 104 may utilize a short-range wireless technology, a Bluetooth standard, a Bluetooth low energy (BLE) standard, a wireless local area network (WLAN) standard, a Wi-Fi (or WiFi) standard, a IEEE (Institute of Electrical and Electronics Engineers) 802.11 standard or its evolution versions (IEEE 802.11ac etc.), for example), a proprietary short-range radio technology.

The term 'processor' 110 refers to a device that is capable of processing data. Depending on the processing power needed, the apparatus 100 may comprise several processors 110 such as parallel processors or a multicore processor. When designing the implementation of the processor 110, a person skilled in the art will consider the requirements set for the size and power consumption of the apparatus 100, the necessary processing capacity, production costs, and production volumes, for example. The processor 110 and the memory 120 may be implemented by an electronic circuitry.

The term 'memory' 120 refers to a device that is capable of storing data run-time (=working memory) or permanently (=non-volatile memory). The working memory and the non-volatile memory may be implemented by a random-access memory (RAM), dynamic RAM (DRAM), static RAM (SRAM), a flash memory, a solid state disk (SSD), PROM (programmable read-only memory), a suitable semiconductor, or any other means of implementing an electrical computer memory.

In an example embodiment, a system clock 118 constantly generates a stream of electrical pulses, which cause the various transferring operations within the apparatus 100 to take place in an orderly manner and with specific timing.

In an example embodiment, the processor 110 may be implemented as a microprocessor implementing functions of a central processing unit (CPU) on an integrated circuit. The CPU is a logic machine executing a computer program code 122. The computer program code 122 may be coded as a computer program using a programming language, which may be a high-level programming language, such as C, or Java, or a low-level programming language, such as a machine language, or an assembler. The CPU may comprise a set of registers 112, an arithmetic logic unit (ALU) 114, and a control unit (CU) 116. The control unit 116 is controlled by a sequence of the computer program code 122 transferred to the CPU from the (working) memory 120. The control unit 116 may contain a number of microinstructions for basic operations. The implementation of the microinstructions may vary, depending on the CPU design. The microprocessor 110 may also have an operating system (a dedicated operating system of an embedded system, a real-time operating system, or even a general-purpose operating system), which may provide the computer program code 122 with system services.

A non-exhaustive list of implementation techniques for the processor 110 and the memory 120 includes, but is not limited to: logic components, standard integrated circuits, application-specific integrated circuits (ASIC), system-on-a-chip (SoC), application-specific standard products (ASSP), microprocessors, microcontrollers, digital signal processors, special-purpose computer chips, field-programmable gate arrays (FPGA), and other suitable electronics structures.

The computer program code 122 may be implemented by software and/or hardware. In an example embodiment, the software may be written by a suitable programming language, and the resulting executable code 122 may be stored on the memory 120 and run by the processor 110.

In an example embodiment, the functionality of the hardware may be designed by a suitable hardware description language (such as Verilog or VHDL), and transformed into a gate-level netlist (describing standard cells and the electrical connections between them), and after further phases the chip implementing the processor 110, memory 120 and the code 122 of the apparatus 100 may be fabricated with photo masks describing the circuitry.

In an example embodiment, the processor 110 and the memory 120 of the apparatus 100 are a part of a microcontroller. In an example embodiment, the sensor interface 108, and/or the radio transceiver 104 also belong to the microcontroller.

In an example embodiment, the sensor interface 108, the radio transceiver 104, the processor 110 and the memory 120 are separate entities, communicatively coupled together by an appropriate serial bus, for example. In general interfaces between the various elements may be implemented with suitable interface technologies, such as a message interface, a method interface, a sub-routine call interface, a block interface, an appropriate serial/parallel bus, or any hardware/software means enabling communication between various sub-units of the apparatus 100.

An example embodiment provides a computer-readable medium 128 for the apparatus 100 comprising a computer program comprising the computer program code 122. Said computer program code 122, when loaded into the apparatus 100 and executed in the apparatus 100, causes the apparatus 100 to perform the operations required to implement the described example embodiments. In an example embodiment, the computer program code 122 may be in source code form, object code form, executable file, or in some intermediate form. The computer-readable medium 128 may comprise at least the following: any entity or device capable of carrying computer program code 122 to the apparatus 100, a record medium, a computer memory, a read-only memory, an electrical carrier signal, a telecommunications signal, and a software distribution medium. In some jurisdictions, depending on the legislation and the patent practice, the computer-readable medium 128 may not be the telecommunications signal. In an example embodiment, the computer-readable medium 128 may be a non-transitory computer readable storage medium.

Figure 2:
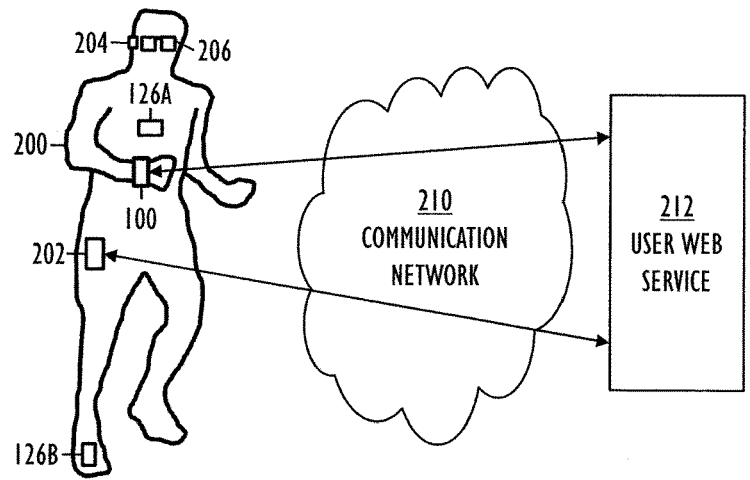

FIG. 2 illustrates an example embodiment where the wearable electronic apparatus 100 is implemented as a running computer, or wrist-worn sports watch, such as designed and manufactured by the Applicant, Polar Electro Oy.

With the wearable electronic apparatus 100, a user 200 may monitor training parameters that characterize the physiological state during the exercise in real-time. The physiological state may be detected from one or more performance metrics, such as by monitoring how the heart rate changes as the training session progresses.

The user 200 is provided with the the wrist-worn apparatus 100. Furthermore, the user 200 may be provided with a heart rate transmitter 126A strapped around the chest, and possibly also with a shoe-mounted stride sensor 126B. The user 200 may also carry a wireless headset 204, and/or smartglasses 206. The accessories 126A, 126B, 204, 206 may communicate wirelessly with the apparatus 100. The wearable electronic apparatus 100 may also interact with a portable apparatus 202 of the user 200.

Various accessories may be flexibly used as needed, i.e. all of them are not necessarily needed all the time, or by all users 200, or in all use cases.

However, in an example embodiment, the apparatus 100 may also be interpreted as a circuitry implementing the required functionality within some suitable equipment.

The apparatus 100 may store the exercise data, which the user (exerciser) 200 may use in post-analysis of the performed exercise. In an example embodiment, the post-analysis is processed in the apparatus 100. In another embodiment, the exercise data is transferred from the wrist-worn apparatus 100 to a user web service 212 through the communication network 210, and the post-analysis is carried out in the user web service 212. If the wrist-worn apparatus 100 does not have a direct Internet access capability, the apparatus 100 may access the Internet (e.g. the user web service 212) via the portable apparatus 202 coupled to the apparatus 100, via a Bluetooth connection, for example. The portable apparatus 202 may be associated to the same user 200 as the apparatus 100.

The user web service 212 may comprise exercise data user accounts (UA), each exercise data user account comprising exercise data associated with a specific user 200. As such, there may be different user accounts for different users. An example embodiment of such a user web service 212 may be a Polar Personal Trainer (PTT), Polar Flow or iFIT service which comprises a database for storing the plurality of user accounts. In an example embodiment, the user web service 212 may require that the user 200 first connects to the user web service 212 by applying a user name and a password, or other identification means. The training/exercise data in the user account may have been stored during or after the exercise. The user account may additionally store physiological data of the user 200 and user attributes obtained from the exerciser 200 and/or the exercise device, such as name, gender, age, weight, height, image, status, motto, fitness level, training schedule, maximum oxygen intake (VO2Max), maximum heart rate (HRMax), performance zones (heart rate zones, speed zones), aerobic and anaerobic thresholds etc.

Figure 3:
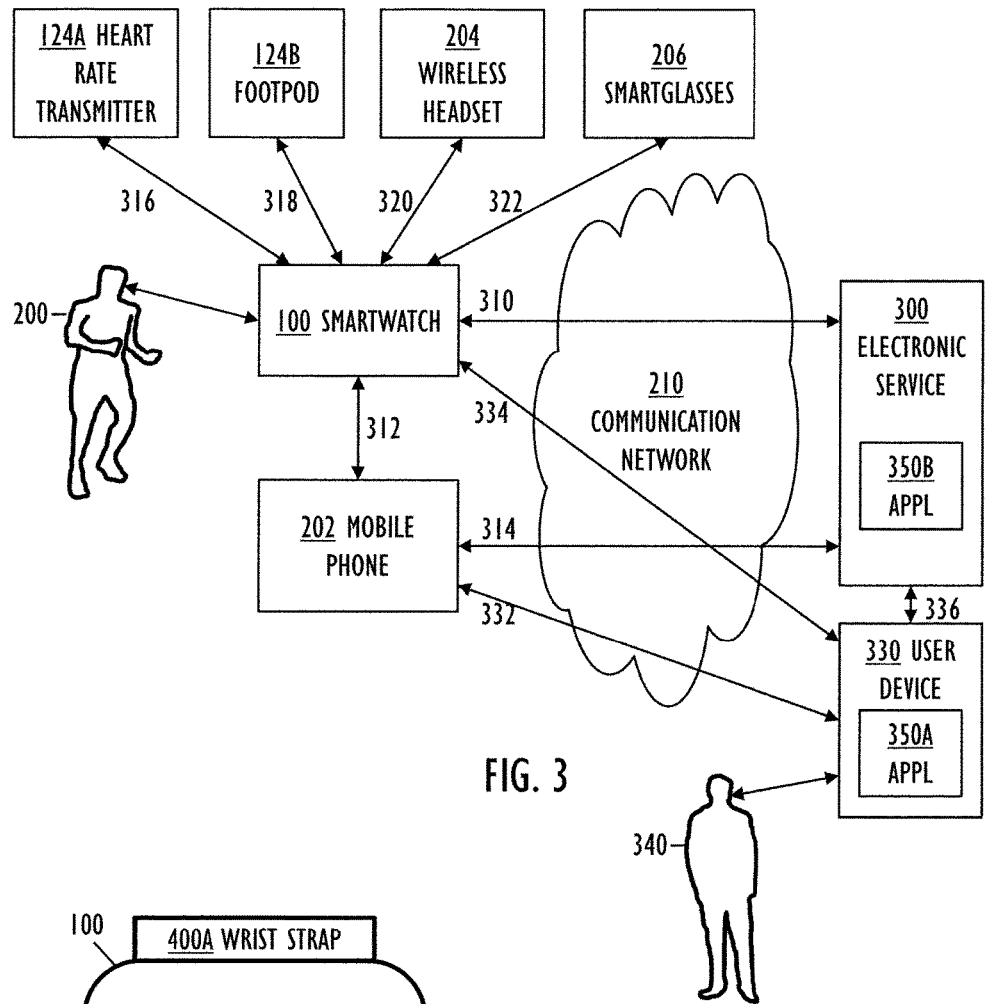

FIG. 3 illustrates further example embodiments of the apparatus 100. The wearable electronic apparatus is implemented as a smartwatch 100, which may be wirelessly communicatively coupled 316, 318, 320, 322 with various accessories 124A, 124B, 204, 206. Additionally, or alternatively, the smartwatch 100 may communicate either directly 310 through the communication network 210 with an electronic service 300, or via 312 the mobile phone 202 and through 314 the communication network 210 with the electronic service 300.

In an example embodiment illustrated in FIG. 3, the portable apparatus 202 is a portable electronic communication apparatus. A non-exhaustive list of the types of the portable apparatus 202 includes: a mobile phone, a smartphone, a tablet computer, a phablet, a general-purpose mobile computing device. In an example embodiment, the portable apparatus 202 is a general-purpose off-the-shelf computing device, as opposed to a purpose-build proprietary equipment, whereby research & development costs will be lower as only the special-purpose software (and not the hardware) needs to be designed, implemented and tested. The portable apparatus 202 may employ a suitable operating system such as iOS, Android, or Windows Phone, for example.

Figure 4:
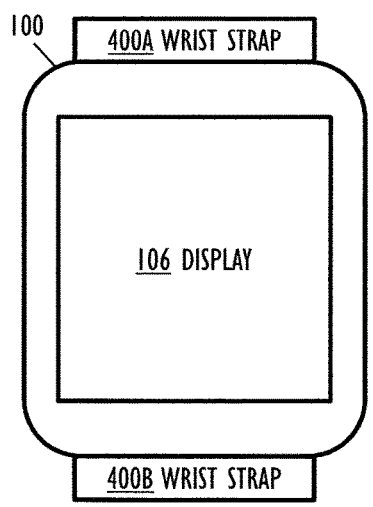

FIG. 4 illustrates further example embodiment of the wearable apparatus 100 being implemented as a wrist-worn apparatus or as a smartwatch.

In an example embodiment, the wearable apparatus 100 comprises a display 106 as at least a part of the user interface. The display 106 may be implemented with suitable technologies including, but not limited to at least the following: a liquid crystal display (LCD), a thin-film transistor (TFT) display, a light-emitting diode (LED) display, an organic LED (OLED) display, an electroluminescent display (ELD), or an electronic paper (or e-paper or electronic ink) display, for example. The display 106 may also incorporate other user interaction means, such as touch input, or haptic feedback, i.e. the display 106 may be a multi-touch display, implemented with resistive or capacitive technology used for touchscreens, for example.

The apparatus 100 may further comprise a wrist strap 400A, 400B for attaching the apparatus 100 to the wrist of the user 200.

Besides the display illustrated in FIG. 4, the wearable electronic apparatus 100 may comprise other user interface elements as well, implementing exchange of graphical, textual and/or auditory information with the user 200. The user interface 106 may be realized with various techniques, such as the display, means for producing sound, a keyboard, and/or a keypad, for example. The means for producing sound may be a loudspeaker or a simpler means for producing beeps or other sound signals. The keyboard/keypad may comprise a complete (QWERTY) keyboard, a mere numeric keypad or only a few push buttons and/or rotary buttons. In addition, the user interface 106 may comprise other user interface components, for example various means for focusing a cursor (mouse, track ball, arrow keys, touch sensitive area etc.) or elements enabling audio control, or a fingerprint sensor enabling control with a fingerprint pattern of the users 200 finger(s).

In an example embodiment, the apparatus 100 may further comprise an independent energy source 124. In an example embodiment, the energy source 124 may be an electric battery converting stored chemical energy into electrical energy. The electric battery 124 may be rechargeable. In an example embodiment, the apparatus 100 may comprise a power interface to receive electrical energy for charging the battery 124. The power interface may couple the apparatus 100 to mains electricity, to a charger connector in a vehicle, or to some other power source enabling the charging of the battery 124. In addition to, or instead of, the battery 124, the apparatus 100 may comprise another portable energy source such as a solar cell 124 converting the energy of light directly into electricity by the photovoltaic effect, or a a fuel cell 124 converting the chemical energy from a fuel into electricity through a chemical reaction with oxygen or another oxidizing agent.

Figure 5A:
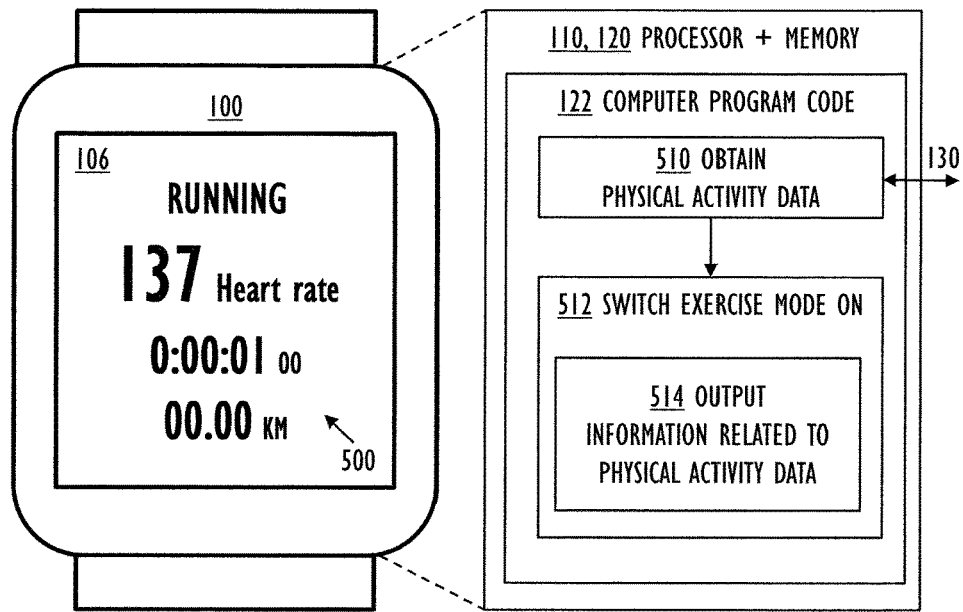
FIGS. 5A and 5B illustrate example embodiments of a user interface of the wearable electronic apparatus.
Figure 5B:
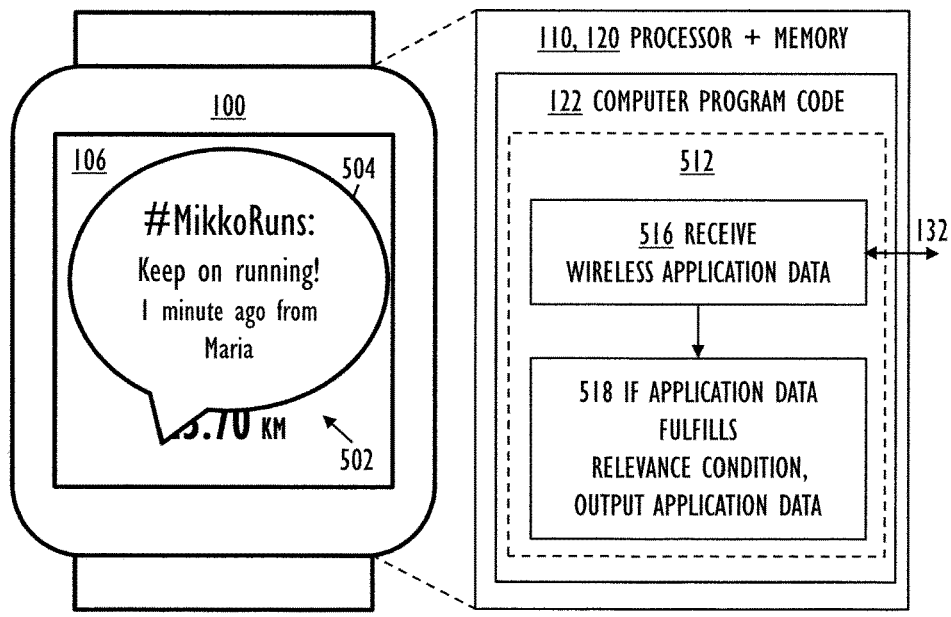

Now that the basic structures of the wearable electronic apparatus 100 have been explained, let us turn to FIGS. 5A and 5B, which illustrate dynamic aspects of the information processing.

In an example embodiment, the one or more memories 120 and the computer program code 122 of the apparatus 100 are configured to, with the one or more processors 110 of the apparatus 100, cause the apparatus 100 to obtain 510, with the sensor interface 108, physical activity data 130 measured relating to the user 200 of the wearable electronic apparatus 100.

The apparatus 100 is also caused to switch 512 an exercise mode of the apparatus 100 on such that information related to the physical activity data 130 is outputted 514, with the user interface 106, to the user 200.

As shown in FIG. 5A, the display 106 shows the physical activity data 130, 500: the apparatus 100 has detected that the user 200 is "running", the heart rate is 136 bpm, the elapsed time is just one second and the mileage is still zero, as the user 200 has just started the exercise.

In FIG. 5B, the exercise of the user 200 has progressed. In an example embodiment, the apparatus 100 is further caused, while the exercise mode is on 512, to receive 516, with the radio transceiver 104, application data 132, and, only if the application data fulfills a predetermined relevance condition, output 518, with the user interface 106, the application data 132 to the user 200. In an example embodiment, the output 518 of the application data 132 is performed with the display 106: "#MikkoRuns: Keep on running", which is a tweet received one minute ago from Maria. Alternatively, or additionally, the application data 132 may be outputted 518 to a display in the smartglasses 206.

In addition to, or instead of, outputting 518 the application data 132 visually, the application data 132 may also be outputted by a (synthesized) voice (with a so-called text-to-speech functionality, for example), by a loudspeaker in the apparatus 100 or in the wireless headset 204 (or even in the portable apparatus 202), for example. The outputting 518 of the application data 132 may be accompanied by further effects (visual or auditory, for example). In an example embodiment, the outputting 518 of the application data 132 may be accompanied by vibration, i.e. the apparatus 100 may comprise a small electric motor connected to an off-center weight, or a solenoid, for example, to generate the vibration.

In an example embodiment illustrated in FIG. 3, the application data 132 originates from an (software) application 350A, 350B residing somewhere else than in the apparatuses 100, 126A, 126B, 202, 204, 206 carried by the user 200. The application 350A, 350B may thus be located in a single resource 300/330 or it may be distributed among a plurality of resources 300, 330.

In an example embodiment, the application data 132 may be addressed to the user 200 from some other person 340, i.e. the application data 132 realizes wireless electronic communication from the other person 340 to the user 200.

As shown in FIG. 3, the application 350A may be located in a user device 330 of the other person 340, and/or the application 350B may be located in an electronic service 320. The user device 330 and/or the electronic service 300 may be communicatively coupled with the wearable apparatus 100 and/or the portable apparatus 202 through the communication network 210.

In an example embodiment, the electronic service 300 may be implemented by a suitable computing resource or a combination of various computing resources.

In an example embodiment, the computing resource 300 may be implemented as a single server computer or as a cluster of computers. The server is a part of the client-server computing model that acts as distributed application which partitions tasks or workloads between the provider of a resource or service, called server, and the service requester, called client. The server 300 may serve a number of apparatuses 100, 202. The server computer 300 may be a host that is running one or more server programs which share their resources with clients 100, 202. The client 100, 202 may request a service function or content from the server 300. Also, the client 100, 202 may initiate a communication session with the server 300 which awaits incoming requests.

In an example embodiment, the electronic service 300 may also operate according to the cloud computing model, at least in part. Naturally, besides these example embodiments of the electronic service 300, other feasible computing architectures may be utilized as well to implement the hardware and software of the electronic service 300. Consequently, besides operating according to the client/server architecture, push technology may be utilized as well. In push technology, the request for a transaction is initiated by the electronic service 300, whereas with the pull technology the request for the information is initiated by the client 100, 202.

In an example embodiment, the application data 132 comprises one or more of the following: a notification from a social media application, a message from an electronic mail application, a notification from a web service, a message from a web service. As shown in FIG. 3, the social media application, the electronic mail application, and/or the web service may be implemented by the application 350A running in the user device 330 and/or the application 350B running in the electronic service 300.

The social media application 350A, 350B implements a computer-mediated tool allowing users 200, 340 to create, share and exchange information (application data 132, and possibly also physical activity data 130 as will be later explained).

In an example embodiment, the application 350A, 350B is Twitter®, which is an online social networking service that enables users 200, 340 to send and read messages ("tweets").

Let us now return to FIG. 5B: the apparatus 100 receives the tweet "#MikkoRuns: Keep on running" from the other person 340. In an example embodiment, the application data 132 (=tweet) is created by the other person 340 with the mobile application (or with a website interface or with a Short Message Service SMS message) 350A in the user device 330, and the application data 132 is then communicated 336 to the database application 350B in the electronic service 300, which then registers the tweet under an unique identifier, adds geolocation data and stores the tweet. The tweet may be public (in which case it is sent to search engines) or it may be private. In either case, the apparatus 100 may obtain the application data 132 (=tweet) and present it to the user 200.

Figure 8:
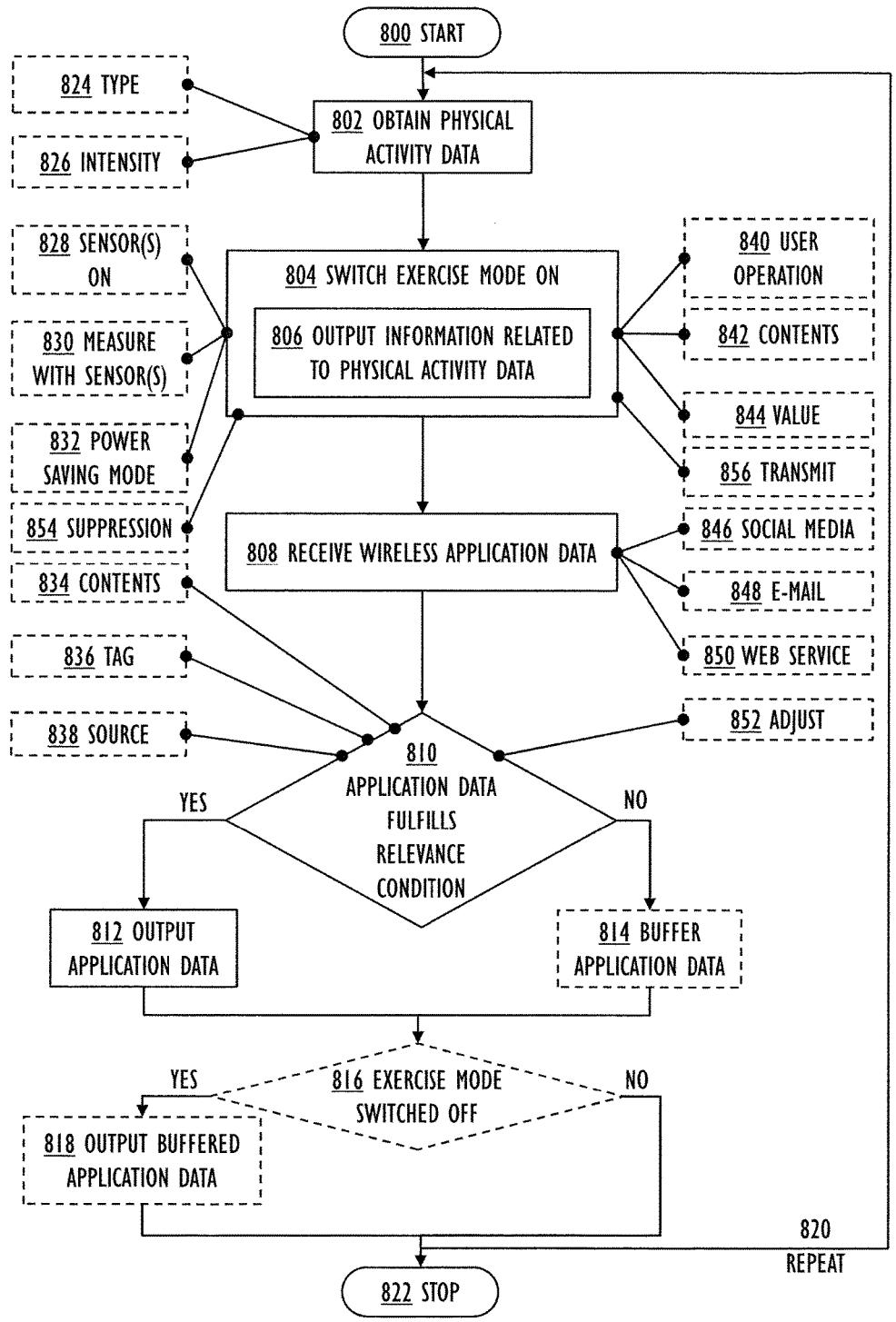
FIG. 8 is a flow-chart illustrating further example embodiments.

Next, let us study FIG. 8, which is a flow chart illustrating further example embodiments. The operations are not strictly in chronological order, and some of the operations may be performed simultaneously or in an order differing from the given ones. Other functions may also be executed between the operations or within the operations and other data exchanged between the operations. Some of the operations or part of the operations may also be left out or replaced by a corresponding operation or part of the operation. It should be noted that no special order of operations is required, except where necessary due to the logical requirements for the processing order. In an example embodiment, the method illustrated in FIG. 8 may be implemented by an electronic apparatus. In an example embodiment, the method may be implemented by the described wearable electronic apparatus 100.

The method starts in 800.

In 802, physical activity data measured relating to a user of a wearable electronic apparatus is obtained.

In 804, an exercise mode of the wearable electronic apparatus is switched on such that information related to the physical activity data is outputted to the user in 806.

While the exercise mode is on, wireless application data is received in 808. Only if the application data fulfills a predetermined relevance condition, which may be tested in 810, the application data is outputted to the user in 812.

The method ends in 822, or, alternatively, the operations 802-804-806-808-810-812 and the supplementary operations may be repeated 820 as required.

The already described example embodiments of the apparatus 100 may be utilized to enhance the method with various further example embodiments.

Next, let us study further example embodiments with reference to FIG. 8.

In an example embodiment, the application data 132 fulfills the predetermined relevance condition in 810 if contents 834 of the application data 132 fulfill the predetermined relevance condition.

In an example embodiment, the contents 834 of the application data 132 may refer to any code or a string included in the application data 132.

The code may be an alphanumeric code, for example. The code may be globally unique or only unique within a certain specified environment. In any case, the code is such that the apparatus 100 is able to interpret the code in order to decide whether the predetermined relevance condition is fulfilled in 810: it may be checked whether the code is according to a predetermined pattern or whether the code exceeds or goes under a preset threshold value.

The string may be written in a natural language or in some other language following a set of rules. The string may comprise characters including letters, numerical digits, punctuation marks and whitespace, for example. The natural language in this context is an ordinary language arising, unpremeditated, in the brains of human beings. Human beings use the natural language to communicate with each other by writing (and by speech). Natural languages include English, Finnish, German etc. In any case, the string is such that the apparatus 100 is able to interpret the string in order to decide whether the predetermined relevance condition is fulfilled in 810: it may be checked whether the string communicates a predetermined idea, or whether the string contains a predetermined sequence of characters, for example.

In an example embodiment, the application data 132 fulfills the predetermined relevance condition in 810 if a tag 836 in the application data 132 fulfills the predetermined relevance condition. In an example embodiment, the tag may refer to one or more of the following: a label of the application data 132, a header of the application data 132, descriptive metadata of the application data 132, a hashtag of the application data 132. The hashtag is a type of label or metadata tag used on social network and microblogging services. The user 200, 340 may create the hashtag by placing the hash character # in front of a word or unspaced phrase, in our example #MikkoRuns. By searching for the hashtag #MikkoRuns, each message tagged with it will be found. If Twitter is used, for example, #MikkoRuns may be used to tag each tweet relating to Mikko running a marathon.

In an example embodiment, the application data 132 fulfills the predetermined relevance condition in 810 if a source 838 of the application data 132 fulfills the predetermined relevance condition. In an example embodiment, the source 838 of the application data 132 may identify the sender or creator of the notification or message containing the application data 132. In an example embodiment, the source 838 may be one or more of the following: a username of the other person 340, an electronic mail address of the other person 340, an IP (Internet Protocol) address of the other person 340, an electronic identifier of the other person 340. If Twitter is used, the source 838 is a verified Twitter account formally validating the identity of the other person 340, or even a company owning the Twitter account.

In a way, the contents 834 and/or the tag 836 and/or the source 838 of the application data 132 serve as a "key", which opens a "trapdoor" enabling the application data 832 to reach the user 200 even during the exercise mode switched on, when the user 200 does not normally want to be disturbed.

Figure 6:
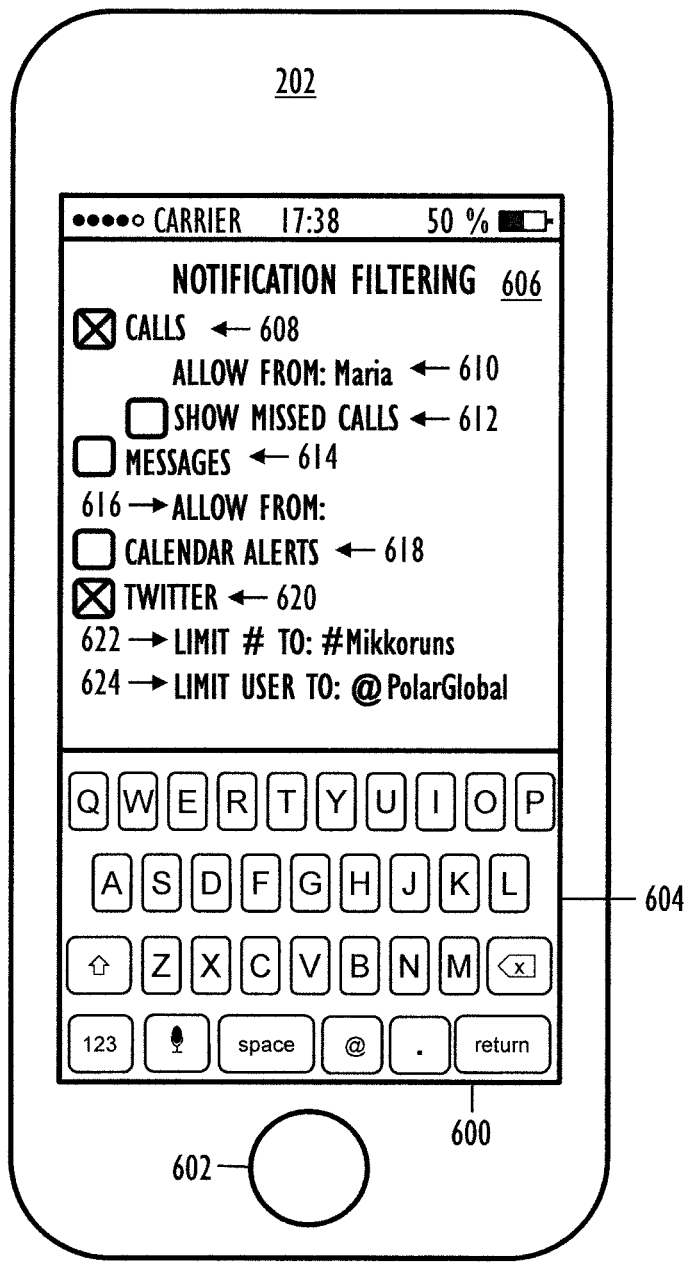
FIG. 6 illustrates example embodiments of a portable apparatus of the user.

With reference to FIG. 6, an example embodiment of the user interface of the portable apparatus 202 is illustrated. The portable apparatus 202 includes a touch screen 600, a button 602, and a virtual keyboard 604. As shown in FIG. 6, a notification filtering window 606 is displayed. The user 200 has allowed calls 608 from Maria 610 and messages 614 from no one 616. Showing 612 of missed calls is not allowed. Calendar alerts 618 are neither allowed. Twitter 620 tweets are allowed from the hashtag #MikkoRuns 622, and from the user @PolarGlobal 624. With this example embodiment, the user 200 manipulates the predetermined relevance condition in the portable apparatus 202, but a similar manipulation may also be implemented to the user interface 106 of the apparatus 100.

In an example embodiment, the exercise mode is switched on in 804 by an operation 840 performed by the user 200 with the user interface 106. Such user-initiated operation 840 may include, for example, pressing a button of the apparatus 100, tapping a touch screen 106 of the apparatus 100, or any other operation of a user interface element in the user interface 106.

In an example embodiment, the exercise mode is switched on automatically in 804 on the basis of contents 842 of the physical activity data 130. Such automatic switching may be based on detecting a start of a reception of physical activity data 130 from any of the sensors 102, 126 through the sensor interface 108.

In an example embodiment, the exercise mode is switched on automatically in 804, if a predetermined value 844 in the physical activity data 130 exceeds a predetermined activity threshold value. Such activity threshold value may relate to any sports-, exercise-, or activity-related parameter, including, but not being limited to hear rate of the user 200, speed of the user 200, cadence of a bike used by the user 200 etc.

In an example embodiment, a type 824 of a physical activity performed by the user 200 is recognized on the basis of contents of the physical activity data 130, and the predetermined relevance condition of 810 is adjusted on the basis of the type 824 of the physical activity. With this example embodiment, it is acknowledged that different types 824 of physical activity (different sports, different exercises, different activities) require varying grades of concentration of the user 200. For example, while walking the user 200 is not heavily loaded, whereupon the predetermined relevance condition may be more relaxed allowing even irrelevant application data 132 to come through, whereas during running (or bicycling or swimming) the predetermined relevance condition needs to be stricter so that the user 200 is not bothered with uninteresting application data 132.

In an example embodiment, the type 824 of the physical activity is recognized on the basis of recognizing a sensor 102, 126 configuration generating the physical activity data 130 for the sensor interface 108. For example, if the physical activity 130 starts to come from a footpod 124B, it may be detected that the user 200 will be running. Alternatively, it could be detected that the user 200 will be walking. Furthermore, the recognition of the type of the physical activity may at least partly be based on history information: if the user 200 has always been running while wearing the footpod 124B, then it is recognized that the user 200 will (again) run, and not walk, for example.

In an example embodiment, an intensity 826 of a physical activity performed by the user 200 is detected on the basis of the physical activity data 130, and the predetermined relevance condition in 810 is adjusted on the basis of the intensity 826 of the physical activity. For example, while jogging slowly, the user 200 is not heavily loaded, whereupon the predetermined relevance condition may be more relaxed, whereas during running fast the predetermined relevance condition is made stricter. In such a scenario, the higher the running speed of the user 200, the higher the perceived intensity 826 for the user 200. Another intensity 826 measure may be heart rate of the user 200: the higher the heart rate, the higher the intensity 826 of the physical activity.

In an example embodiment, while the exercise mode is on, the apparatus 100 is further caused to perform one or more of the following:

switch 828 one or more sensors 102, 126, 124A, 124B on in order to measure the physical activity data 130;

measure 830 the physical activity data 130 with one or more sensors 102, 126, 124A, 124B;

switch operation of the apparatus 100 on a power saving mode 832.

In an example embodiment, the apparatus 100 supports a normal operation mode and a power saving (or limited) operation mode 832. The power consumption of the apparatus 100 during the power saving operation mode 832 may be smaller for a given task than during the normal operation mode. In an example embodiment, during the power saving operation mode 832, the functionalities of the apparatus 100 are available through an operating system of the apparatus 100. The operating system may comprise a plurality of layers including a kernel and library function-layer. During the power saving operation mode, the apparatus 100 may execute algorithms by applying a direct low-level hardware access bypassing at least the layers of the operating system that are above the kernel and the library function-layer. This example embodiment is illustrated in more detail in Applicant's other application published as WO 2015/024674, incorporated herein by reference.

In an example embodiment, if the exercise mode is on, a suppression message 854 is transmitted with the radio transceiver 104 from the apparatus 100, the suppression message instructing that a recipient of the suppression message 854 is not allowed to transmit the application data 132 as the exercise mode is on, wherein the recipient is one or more of the following: the portable apparatus of the user 202, the electronic service 300. Basically, with this example embodiment, the scarce energy source 124 of the apparatus 100 may further be saved, as the portable apparatus 100 does not then need to receive application data 132 during the exercise mode being on. If the exercise mode is switched off, then a cancel message may be transmitted to the recipient 202 and/or 300, whereupon the transmission of the application data 132 may be resumed.

In an example embodiment, if the exercise mode is switched off, the application data 132 is outputted, with the user interface 106, regardless of the predetermined relevance condition. With this example embodiment, the predetermined relevance condition no more applies as the user 200 no more engages in demanding physical activity.

In an example embodiment, if the exercise mode is on, the apparatus 100 is caused to buffer 814 such application data 132 that does not fulfill the predetermined relevance condition in 810, and, after the exercise mode is switched off in 816, to output 818, with the user interface 106, the buffered application data 132 regardless of the predetermined relevance condition. With this example embodiment, the application data 132 collected during the exercise mode being on may be presented to the user 200, i.e., no application data 132 will be lost as it is stored in the (temporary) buffer, in the memory 120, for example.

In an example embodiment, the apparatus 100 is further caused to, while the exercise mode is on, if a predetermined transmit condition is fulfilled, transmit 856, with the radio transceiver 104, the information related to the physical activity data 130 to the electronic service 300. With this example embodiment, the user 200 may during the physical activity automatically or semi-automatically transmit information about the physical activity to the electronic service 300, whereby the information may be shared with the other user 340, through the social media application, the electronic mail application, and/or the web service, for example.

Figure 9:
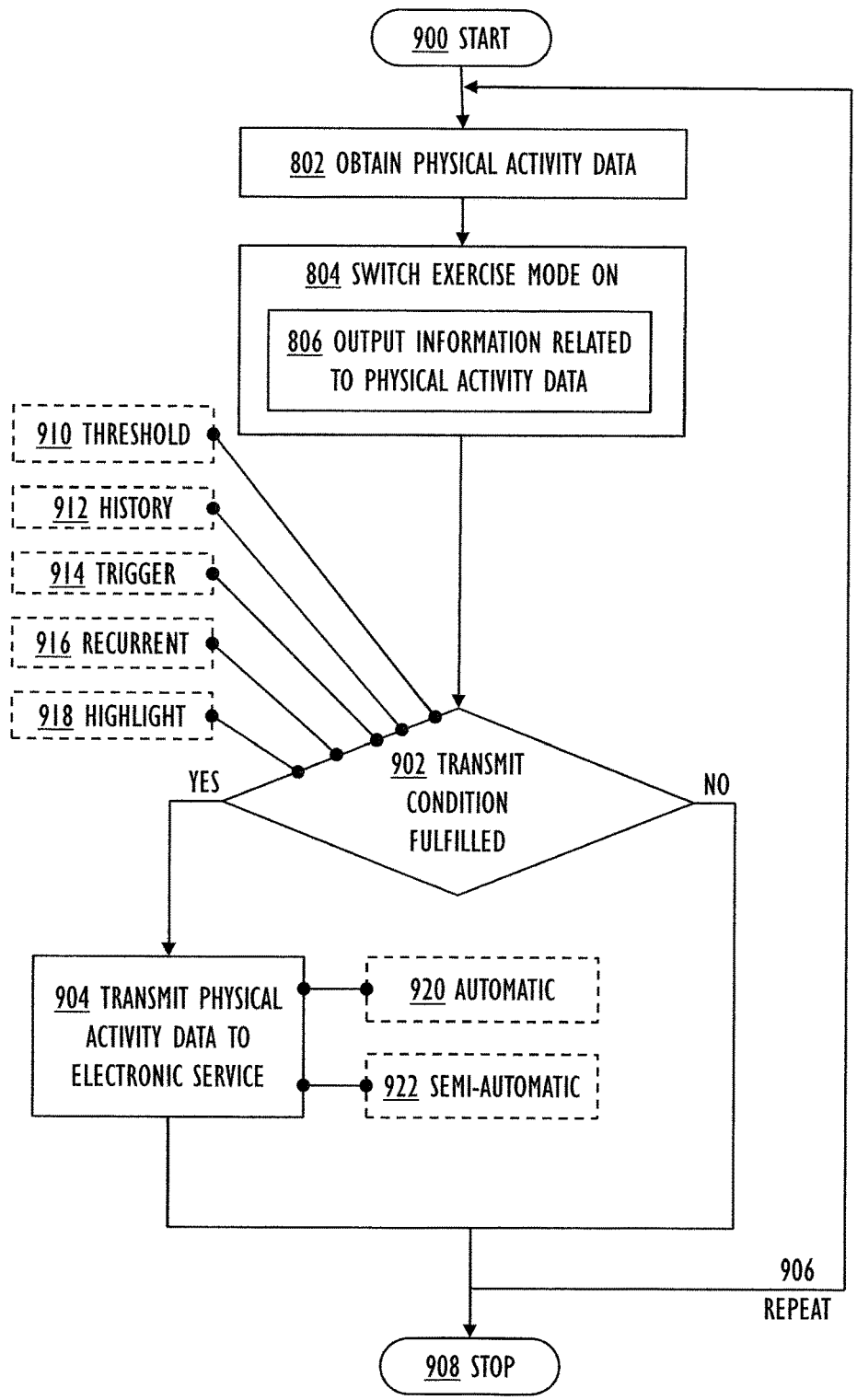
FIG. 9 is a flow-chart illustrating alternate example embodiments.

Next, let us study FIG. 9, which is a flow chart illustrating further example embodiments. These example embodiments relate to the example embodiment of 856 in FIG. 8. However, it is to be noted that the example embodiments illustrated in FIG. 9 may also be utilized independent of the earlier example embodiments, i.e., the basic example embodiment only includes operations 802-804-806-902-904. The method illustrated in FIG. 9 may be implemented by an electronic apparatus.

In an example embodiment, the method may be implemented by the described wearable electronic apparatus 100. In this example embodiment, a wearable electronic apparatus 100 comprises a user interface 106; a radio transceiver 104; a sensor interface 108; one or more processors 110; and one or more memories 120 including computer program code 122, the one or more memories 120 and the computer program code 122 configured to, with the one or more processors 110, cause the apparatus 100 at least to: obtain, with the sensor interface 108, physical activity data 130 measured relating to a user 200 of the wearable electronic apparatus 100; switch an exercise mode of the apparatus 100 on such that information related to the physical activity data 130 is outputted, with the user interface 106, to the user 200; and, while the exercise mode is on, if a predetermined transmit condition is fulfilled, transmit, with the radio transceiver 104, the information related to the physical activity data 130 to an electronic social media service 300.

The method starts in 900.

In 802, physical activity data measured relating to a user of a wearable electronic apparatus is obtained.

In 804, an exercise mode of the wearable electronic apparatus is switched on such that information related to the physical activity data is outputted to the user in 806.

While the exercise mode is on, if a predetermined transmit condition is fulfilled in 902, the information related to the physical activity data is transmitted 904 wirelessly to the electronic social media service 300, 350B, 350A. The electronic social media service may include, but is not limited to Twitter® and/or Facebook®.

The method ends in 908, or, alternatively, the operations 802-804-806-902-904 and the supplementary operations may be repeated 906 as required.

The already described example embodiments of the apparatus 100 may be utilized to enhance the method with various further example embodiments.

Figure 7:
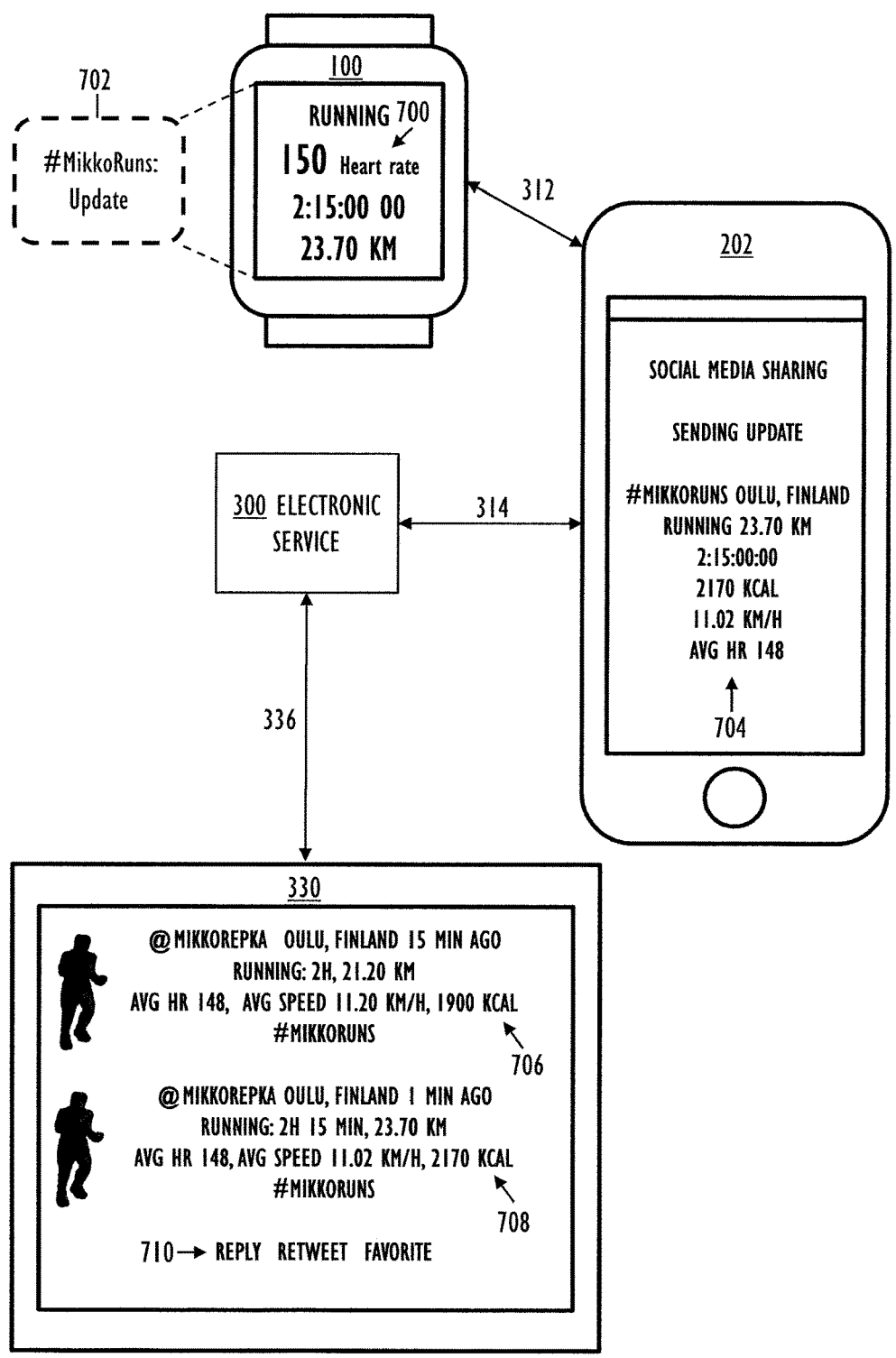
FIG. 7 illustrates example embodiments of a communication between the wearable electronic apparatus, the portable apparatus, an electronic service, and a user device of another user.

Next, let us study further example embodiments with reference to FIGS. 7 and 9.

The user 200 has paired the wearable apparatus 100 with the portable apparatus 202 such that the real-time connectivity is also available during the physical activity. The user 200 has also added favorite social media accounts to his Polar app, which is allowed to create posts. The user 200 may set real-time social media sharing on and set whether the information is shared automatically 920 or semi-automatically 922. If the automatic 920 sharing is on, the wearable apparatus 100 and/or the portable apparatus 202 perform the posting automatically, or in the semi-automatic 922 mode the user 200 is required to initiate and/or confirm 702 the transmission 312, 314 with the user interface 106. In the example embodiment of FIG. 7, the initiation/confirmation may be performed by tapping the window 702 shown on the display 106.

The transmit condition in 902 may be fulfilled in various ways.

In an example embodiment, the transmit condition is fulfilled if a parameter related to the physical activity data meets a predetermined threshold 910. The parameter may be physiological parameter (heart rate, speed, performance intensity, body temperature etc.) or it may relate in some other way to the physical activity.

In an example embodiment, the transmit condition is fulfilled if a parameter related to the physical activity data meets a predetermined history condition 912. For example: the user 200 arrives at a geographical location where s/he has been in the past as well.

In an example embodiment, the transmit condition is fulfilled if a parameter related to the physical activity data meets a predetermined trigger condition 914. The parameter may relate to an elapsed time or distance, such as after one hour or after 10 kilometers or miles, for example.

In an example embodiment, the transmit condition is fulfilled if a parameter related to the physical activity data meets a predetermined recurrent condition 916. The parameter may relate to elapsed time, burned calories, distance, laps etc. For example: the post may be made every 30 minutes, after every 200 kcal has been burned, after every 5 kilometers or miles, or after every finished lap.

In an example embodiment, the transmit condition is fulfilled if a parameter related to the physical activity data meets a predetermined highlight condition 918. The highlight may relate to a specific and/or dramatic event: start of the physical activity, end of the physical activity, manually pressed lap time etc.

In the example embodiment of FIG. 7, the wearable apparatus 100 has gathered the physical activity data 700, which is then communicated 312 to the portable apparatus 202, which may (in our example embodiment by displaying "SOCIAL MEDIA SHARING" and the contents of the collected physical activity data 130) or may not indicate 704 the transmission 314 of the post to the electronic service 300. The electronic service 300, for example the application 350B, may then communicate 336 the information to the user device 330. As shown, the user device 330 may display the previous tweet 706 and the current tweet 708. The other person 340 may then perform further actions 710: reply to the tweet 708, retweet the tweet 708, or mark the tweet 708 as a favorite, for example. The user 200 may have selected predefined texts (such as hashtags) to start the post. The portable apparatus 202 may add further information: location text may be obtained from a map service, for example. The post may include varying information (depending on social media limitations), such as: location, sport name, distance, elapsed time, burned calories, average speed, average heart rate etc.

It will be obvious to a person skilled in the art that, as technology advances, the inventive concept can be implemented in various ways. The invention and its embodiments are not limited to the example embodiments described above but may vary within the scope of the claims.

The invention claimed is:

1. A wearable electronic apparatus comprising:
a user interface;
a radio transceiver;
a sensor interface;
one or more processors; and
one or more memories including computer program code, the one or more memories and the computer program code configured to, with the one or more processors, cause the apparatus at least to perform operations comprising:
obtaining, with the sensor interface, physical activity data measured relating to a user of the wearable electronic apparatus;
switching an exercise mode of the apparatus on such that information related to the physical activity data is outputted, with the user interface, to the user;
while the exercise mode is on, receiving, with the radio transceiver, application data, and, only if the application data fulfills a predetermined relevance condition, outputting, with the user interface, the application data to the user, the application data comprising a message from a web service, and
determining the predetermined relevance condition based on a tag in the application data fulfilling the predetermined relevance condition,
wherein the tag refers to at least one of a hashtag of the application data, a type of label tag used on social network and microblogging services, a type of metadata tag used on social network and microblogging services, wherein, if the exercise mode is on, a suppression message is transmitted using the radio transceiver, the suppression message instructing a recipient device of the suppression message not to transmit the application data, wherein the recipient device is one or more of the following: a portable apparatus of the user, an electronic service, wherein, if the exercise mode is off, a cancel message is transmitted using the radio transceiver, the cancel message instructing the recipient device of the cancel message resume transmission of the application data.

2. The apparatus of claim 1, wherein the application data comprises a notification from a social media application.

3. The apparatus of claim 1, wherein the application data fulfills the predetermined relevance condition if contents of the application data fulfill the predetermined relevance condition.

4. The apparatus of claim 1, wherein the application data fulfills the predetermined relevance condition if a source of the application data fulfills the predetermined relevance condition.

5. The apparatus of claim 1, wherein the exercise mode is switched on by an operation performed by the user with the user interface.

6. The apparatus of claim 1, wherein the exercise mode is switched on automatically on the basis of contents of the physical activity data.

7. The apparatus of claim 1, wherein the exercise mode is switched on automatically if a predetermined value in the physical activity data exceeds a predetermined activity threshold value.

8. The apparatus of claim 1, wherein a type of a physical activity performed by the user is recognized on the basis of contents of the physical activity data, and the predetermined relevance condition is adjusted on the basis of the type of the physical activity.

9. The apparatus of claim 8, wherein the type of the physical activity is recognized on the basis of recognizing a sensor configuration generating the physical activity data for the sensor interface.

10. The apparatus of claim 1, wherein an intensity of a physical activity performed by the user is detected on the basis of the physical activity data, and the predetermined relevance condition is adjusted on the basis of the intensity of the physical activity.

11. The apparatus of claim 1, wherein, while the exercise mode is on, the apparatus is further caused to perform one or more operations comprising:
switching one or more sensors on in order to measure the physical activity data;
measuring the physical activity data with one or more sensors;
switching operation of the apparatus on a power saving mode.

12. The apparatus of claim 1, wherein the wearable electronic apparatus comprises a smartwatch.

13. The apparatus of claim 1, wherein the radio transceiver comprises a transceiver operating according to one or more of the following: a short-range wireless technology, a Bluetooth standard, a Bluetooth low energy standard, a wireless local area network WLAN standard, a Wi-Fi standard, a IEEE 802.11 standard, a proprietary short-range radio technology.

14. The apparatus of claim 1, wherein the radio transceiver comprises a transceiver interoperating with a cellular radio network.

15. The apparatus of claim 1, wherein, if the exercise mode is switched off, the application data is outputted, with the user interface, regardless of the predetermined relevance condition.

16. The apparatus of claim 1, wherein, if the exercise mode is on, the apparatus is caused to buffer such application data that does not fulfill the predetermined relevance condition, and, after the exercise mode is switched off, to output, with the user interface, the buffered application data regardless of the predetermined relevance condition.

17. The apparatus of claim 1, wherein the operations further comprise:
while the exercise mode is on, if a predetermined transmit condition is fulfilled, transmitting, with the radio transceiver, the information related to the physical activity data to an electronic service.

18. A non-transitory computer-readable storage medium comprising a computer program comprising computer program code which, when executed by a wearable electronic apparatus, causes the apparatus to perform operations comprising:
obtaining physical activity data measured relating to a user of the wearable electronic apparatus;
switching an exercise mode of the wearable electronic apparatus on such that information related to the physical activity data is outputted to the user;
while the exercise mode is on, receiving wireless application data, and, only if the application data fulfills a predetermined relevance condition, outputting the application data to the user, the application data comprising a message from a web service;
determining the predetermined relevance condition based on a tag in the application data fulfilling the predetermined relevance condition,
wherein the tag refers to at least one of a hashtag of the application data, a type of label tag used on social network and microblogging services, a type of metadata tag used on social network and microblogging services, wherein, if the exercise mode is on, a suppression message is transmitted using the radio transceiver, the suppression message instructing a recipient device of the suppression message not to transmit the application data, wherein the recipient device is one or more of the following: a portable apparatus of the user, an electronic service, wherein, if the exercise mode is off, a cancel message is transmitted using the radio transceiver, the cancel message instructing the recipient device of the cancel message resume transmission of the application data.

19. A wearable electronic apparatus comprising:
a user interface;
a radio transceiver;
a sensor interface;
one or more processors; and
one or more memories including computer program code,
the one or more memories and the computer program code configured to, with the one or more processors, cause the apparatus to perform operations comprising:
obtaining, with the sensor interface, physical activity data measured relating to a user of the wearable electronic apparatus;
switching an exercise mode of the apparatus on such that information related to the physical activity data is outputted, with the user interface, to the user;
receiving, with the radio transceiver, while the exercise mode is on, application data, and, only if the application data fulfills a predetermined relevance condition, outputting, with the user interface, the application data to the user, wherein the application data fulfills the predetermined relevance condition if a source of the application data fulfills the predetermined relevance condition, and the source of the application data identifies a sender or creator of a notification or a message containing the application data; and
outputting, if the exercise mode is switched off, the application data with the user interface, regardless of the predetermined relevance condition, wherein, if the exercise mode is on, a suppression message is transmitted using the radio transceiver, the suppression message instructing a recipient device of the suppression message not to transmit the application data, wherein the recipient device is one or more of the following: a portable apparatus of the user, an electronic service, wherein, if the exercise mode is off, a cancel message is transmitted using the radio transceiver, the cancel message instructing the recipient device of the cancel message resume transmission of the application data.

20. A non-transitory computer-readable storage medium comprising a computer program comprising computer program code which, when executed by a wearable electronic apparatus, causes the apparatus to perform operations comprising:
obtaining, with a sensor interface, physical activity data measured relating to a user of the wearable electronic apparatus;
switching an exercise mode of the apparatus on such that information related to the physical activity data is outputted, with a user interface, to the user;
receiving, with a radio transceiver, while the exercise mode is on, application data, and, only if the application data fulfills a predetermined relevance condition, outputting, with the user interface, the application data to the user, wherein the application data fulfills the predetermined relevance condition if a source of the application data fulfills the predetermined relevance condition, and the source of the application data identifies a sender or creator of a notification or a message containing the application data; and outputting, if the exercise mode is switched off, the application data with the user interface, regardless of the predetermined relevance condition, wherein, if the exercise mode is on, a suppression message is transmitted using the radio transceiver, the suppression message instructing a recipient device of the suppression message not to transmit the application data, wherein the recipient device is one or more of the following: a portable apparatus of the user, an electronic service, wherein, if the exercise mode is off, a cancel message is transmitted using the radio transceiver, the cancel message instructing the recipient device of the cancel message resume transmission of the application data.

21. A wearable electronic apparatus comprising:

a user interface;

a radio transceiver;

a sensor interface;

one or more processors; and one or more memories including computer program code, the one or more memories and the computer program code configured to, with the one or more processors, cause the apparatus at least to perform operations comprising:

obtaining, with the sensor interface, physical activity data measured relating to a user of the wearable electronic apparatus;

switching an exercise mode of the apparatus on such that information related to the physical activity data is outputted, with the user interface, to the user;

while the exercise mode is on, receiving, with the radio transceiver, application data, and, only if the application data fulfills a predetermined relevance condition, outputting, with the user interface, the application data to the user, the application data comprising a message from a web service, and determining the predetermined relevance condition based on a tag in the application data fulfilling the predetermined relevance condition, wherein the tag refers to at least one of a hashtag of the application data, a type of label tag used on social network and microblogging services, a type of metadata tag used on social network and microblogging services, wherein an intensity of a physical activity performed by the user is detected on the basis of the physical activity data, and the predetermined relevance condition is adjusted on the basis of the intensity of the physical activity.

22. A wearable electronic apparatus comprising:

a user interface;

a radio transceiver;

a sensor interface;

one or more processors; and one or more memories including computer program code, the one or more memories and the computer program code configured to, with the one or more processors, cause the apparatus to perform operations comprising:

obtaining, with the sensor interface, physical activity data measured relating to a user of the wearable electronic apparatus;

switching an exercise mode of the apparatus on such that information related to the physical activity data is outputted, with the user interface, to the user;

receiving, with the radio transceiver, while the exercise mode is on, application data, and, only if the application data fulfills a predetermined relevance condition, outputting, with the user interface, the application data to the user, wherein the application data fulfills the predetermined relevance condition if a source of the application data fulfills the predetermined relevance condition, and the source of the application data identifies a sender or creator of a notification or a message containing the application data; and outputting, if the exercise mode is switched off, the application data with the user interface, regardless of the predetermined relevance condition, wherein an intensity of a physical activity performed by the user is detected on the basis of the physical activity data, and the predetermined relevance condition is adjusted on the basis of the intensity of the physical activity.

* * * * *